(12) United States Patent
Suzuki et al.

(10) Patent No.: US 7,572,278 B2
(45) Date of Patent: Aug. 11, 2009

(54) ROD CONNECTOR

(75) Inventors: Nobumasa Suzuki, Tokyo (JP); Yutaka Nohara, Koshigaya (JP); Shinnosuke Nakahara, Okayama (JP); Shigenobu Sato, Sapporo (JP); Kazumasa Ueyama, Hirosaki (JP); Kazuhiro Hasegawa, Niigata (JP); Kazuya Oribe, Tokyo (JP); Hiroshi Takamido, Nagoya (JP)

(73) Assignee: Showa Ika Kohgyo Co., Ltd., Aichi (JP)

( * ) Notice: Subject to any disclaimer, the term of this patent is extended or adjusted under 35 U.S.C. 154(b) by 0 days.

(21) Appl. No.: 10/659,297

(22) Filed: Sep. 11, 2003

(65) Prior Publication Data

US 2004/0133202 A1    Jul. 8, 2004

(30) Foreign Application Priority Data

Sep. 12, 2002    (JP) .......................... P2002-267299

(51) Int. Cl.
    *A61B 17/70*    (2006.01)
(52) U.S. Cl. ...................... 606/266; 606/278
(58) Field of Classification Search .................. 606/61, 606/72, 60, 73, 278, 256, 266, 250, 252, 606/253
See application file for complete search history.

(56) References Cited

U.S. PATENT DOCUMENTS

| | | | |
|---|---|---|---|
| 4,611,582 A * | 9/1986 | Duff .............................. | 606/61 |
| 5,098,432 A | 3/1992 | Wagenknecht | |
| 5,254,118 A * | 10/1993 | Mirkovic ...................... | 606/61 |
| 5,545,167 A | 8/1996 | Lin | |
| 5,575,792 A * | 11/1996 | Errico et al. ................... | 606/61 |
| 5,584,831 A * | 12/1996 | McKay ......................... | 606/61 |
| 5,630,817 A * | 5/1997 | Rokegem et al. .............. | 606/61 |
| 5,716,355 A * | 2/1998 | Jackson et al. ............... | 606/252 |
| 5,743,669 A * | 4/1998 | Fujita et al. .................. | 403/131 |
| 5,876,403 A * | 3/1999 | Shitoto ......................... | 606/61 |
| 5,938,663 A * | 8/1999 | Petreto ......................... | 606/61 |
| 6,016,592 A * | 1/2000 | Lavender ...................... | 29/272 |
| 6,063,089 A * | 5/2000 | Errico et al. ................... | 606/61 |
| 6,187,005 B1 * | 2/2001 | Brace et al. ................... | 606/61 |
| 6,309,390 B1 * | 10/2001 | Le Couedic et al. ........... | 606/61 |
| 6,616,668 B2 * | 9/2003 | Altarac et al. ................. | 606/61 |
| 2003/0114853 A1 * | 6/2003 | Burgess et al. ................ | 606/61 |

FOREIGN PATENT DOCUMENTS

| | | |
|---|---|---|
| CH | 668546 | 1/1989 |
| EP | 0425783 | 5/1991 |
| FR | 2759894 | 8/1998 |
| JP | 11318932 | 11/1999 |
| JP | 2000-033091 | 2/2000 |

OTHER PUBLICATIONS

English Language Abstract of JP 11-318932.
English language Abstract of JP 2000-033091.

* cited by examiner

*Primary Examiner*—Pedro Philogene
(74) *Attorney, Agent, or Firm*—Greenblum & Bernstein, P.L.C.

(57) ABSTRACT

A rod connector is provided with a rod supporting portion in a part of a connector main body supported to a leading end of a shank portion. A rod pressing portion is provided in a side opposing to the rod supporting portion, and a rod is clamped and fixed by the rod pressing portion and the rod supporting portion. At this time, small convex portions provided in the rod supporting portion eat into the rod.

5 Claims, 4 Drawing Sheets

ROD CONNECTOR

CROSS REFERENCE TO RELATED APPLICATIONS

This application is based upon and claims the benefit of priority from the prior Japanese Patent Applications No. P2002-267299, filed on Sep. 12, 2002; the entire contents of which are incorporated herein by reference.

BACKGROUND OF THE INVENTION

1. Field of the Invention

The present invention relates to a rod connector for supporting a bone connection rod which connects bones, for example, a breast bone, a lumbar vertebra or the like, and more particularly to a rod connector structured such that a connector main body supporting the rod freely swings with respect to a shank portion attached to an implant, for example, a screw or the like.

2. Description of the Related Art

As shown in FIG. 1, in a conventional bone connecting method, a plurality of screws (implants) 103 is screwed in to a lumbar vertebrae, and each screws 103 is supported by a rod 105 each other. And a conventional rod connector 107 interconnects the screws 103 and the rod 105.

As shown in FIG. 2, the conventional rod connector 107 is comprised of a connector main body 113 integrally formed in a distal end of a shank portion 109 supported by a head portion of the screw 103. The connector main body 113 is provided with a rod insertion hole 111 allowing to freely insert the rod 105 (shown in FIG. 1) and a locking screw 115 for pressure fixing the rod 105.

According to the structure mentioned above, even in the case that a position of the screw 103 is slightly displaced, it is possible to fine adjust the position of the rod connector 107 by adjusting a position of the shank portion 109 and a rotation of the shank portion 109 around an axis thereof with respect to the screw 103, whereby it is possible to properly support the rod 105. However, the rod connector 107 can be adjusted with respect to the screw 103 only in a range that the shank portion 109 can rotate. Accordingly, there is a problem that an adjustable range is small.

Further, according to Japanese Patent Application Laid-Open No. 11-318932, there is disclosed a structure in which a connection device corresponding to the rod connector 107 of the related art mentioned-above is constituted by a plastically deformable member, and a rod is properly supported by plastically deforming the connection device.

In this case, there is also a problem that a freedom of adjusting the rod connector with respect to the screw is small.

BRIEF SUMMARY OF THE INVENTION

The present invention is made by taking the problems mentioned above into consideration, and an object of the present invention is to provide a rod connector in which a position adjustable range is large. To attain this object, a rod connector according to the present invention is comprised of a connector main body swingably attached to a distal end of a shank portion; a rod supporting portion provided in a part of the connector main body and supporting a rod; and a pressure fixing device provided in the connector main body for pressure fixing the rod to the rod supporting portion.

DETAILED DESCRIPTION OF THE INVENTION

Figure 1:
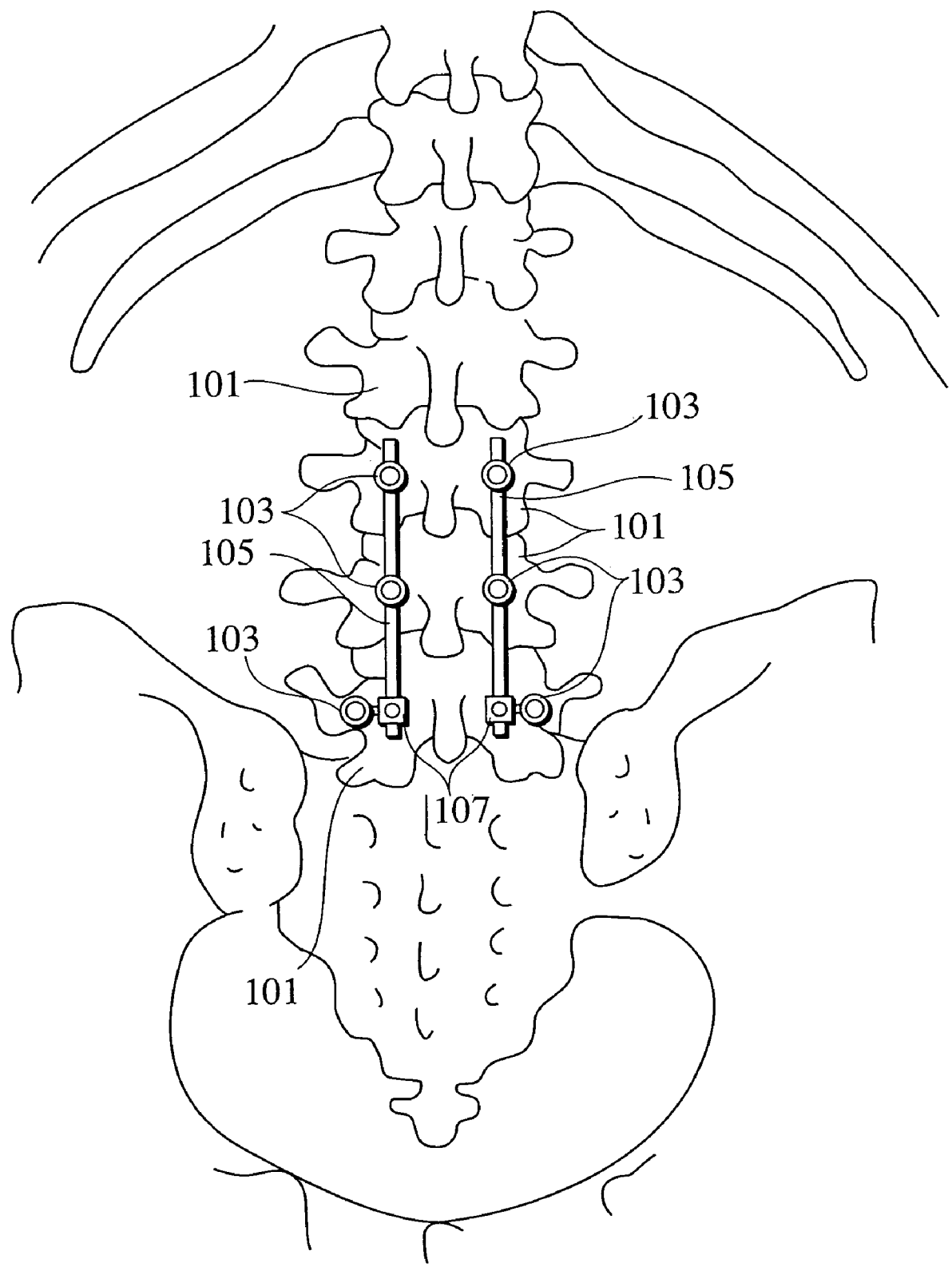
FIG. 1 is a schematic view showing a connection state of a vertebra body by using a conventional rod.
Figure 2:
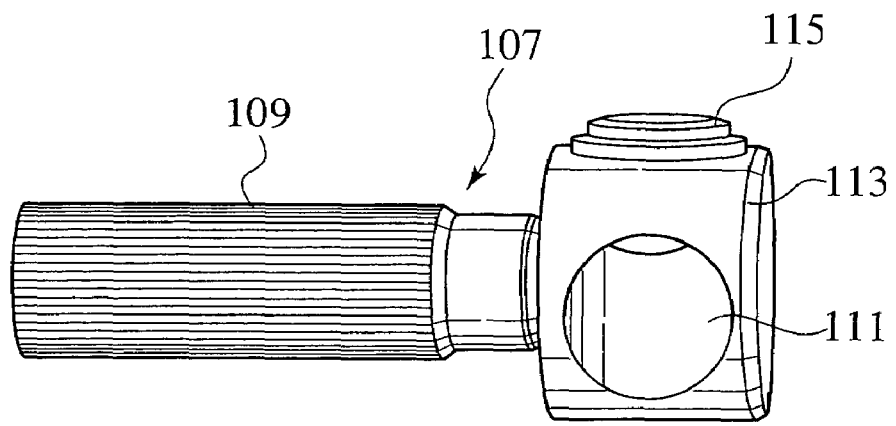
FIG. 2 is a schematic view of a conventional rod connector.
Figure 3:
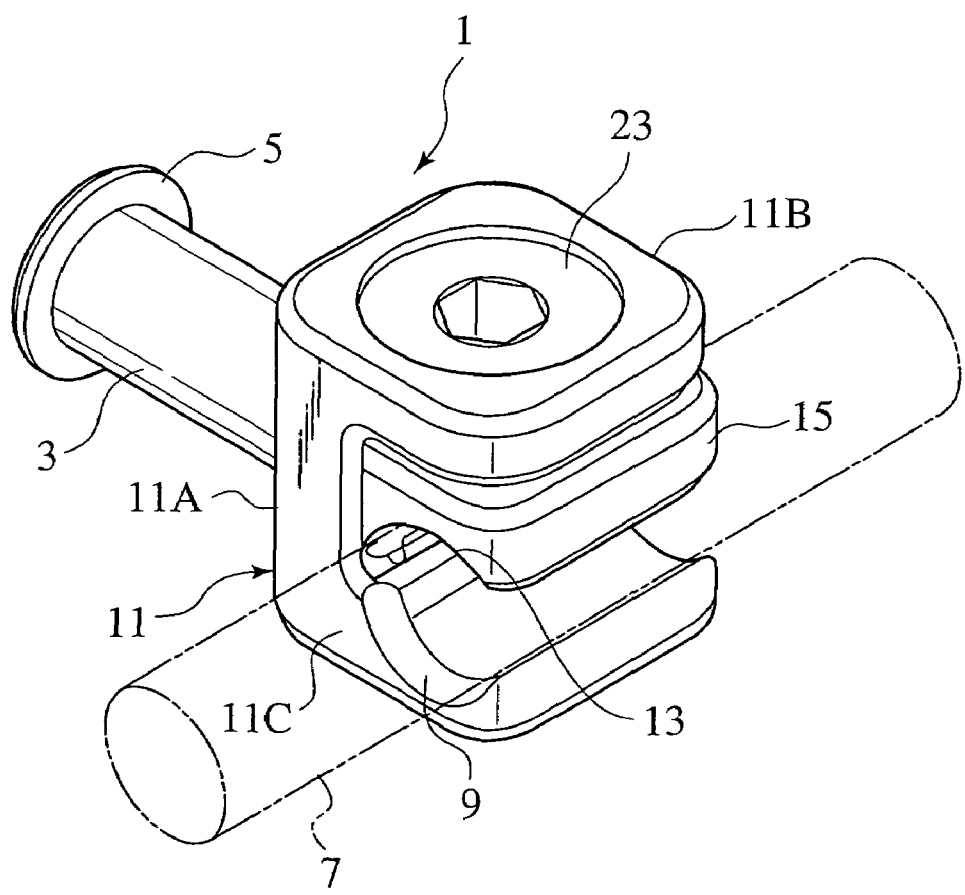
FIG. 3 is a perspective view of a rod connector according to an embodiment of the present invention.
Figure 4:
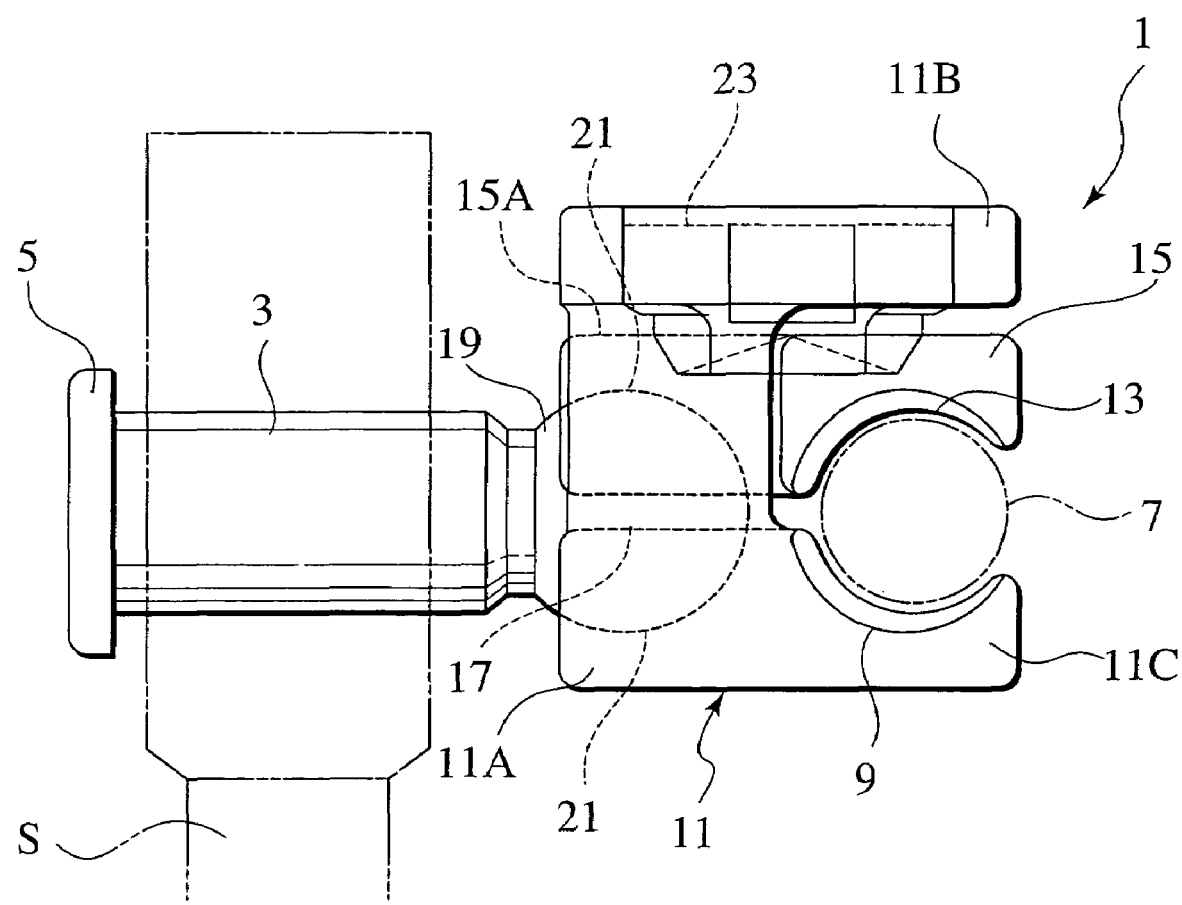
FIG. 4 is a front elevation view of the rod connector according to the embodiment of the present invention.

With reference to FIGS. 3 and 4, a rod connector 1 according to an embodiment of the present invention is provided with a shank portion 3 having a circular cross sectional shape and supported to a U-shaped engagement groove formed in an upper portion of a screw (an implant) S being screwed into a vertebra body (not shown). A rear end portion of the shank portion 3 is provided with a flange portion 5 (a come-off prevention means) for preventing the rod connector 1 from coming off from the U-shaped engagement groove of the screw S in an axial direction.

A connector main body 11 is swingably attached to a distal end portion of the shank portion 3. The connector main body 11 is provided with a rod supporting portion 9 having a circular arc curved shape and supporting a rod 7 for a bone connection connecting vertebra bodies. In more detail, the connector main body 11 is comprised of a base body portion 11A being vertically attached to the shank 3, protruding portions 11B and 11C extended from both upper and lower end sides of the base body portion 11A approximately, and has an approximately C shape. Further, a rod supporting portion 9 is formed on an opposing surface in which the protruding portion 11C opposes to the protruding portion 11B.

In order to pressure fix the rod 7 to the rod supporting portion 9, a rod pressing member 15 provided with a rod pressing portion 13 having a circular arc curved surface and opposing to the rod supporting portion 9 is attached to the connector main body 11 so as to freely move in a direction moving apart from and close to the rod supporting portion 9.

In more detail, a through hole 17 penetrating in a horizontal direction in FIG. 4 is formed in the base body portion 11A, and a base portion 15A of the rod pressing member 15 is engaged within the through hole 17 so as to vertically move. Further, a spherical body portion 19 formed in a distal end portion of the shank portion 3 is attached to the through hole 17. Further, a pair of engagement recess portions 21, 21 is formed in each of a portion in which the base body portion 11A of the connector main body 11 corresponds to the spherical body portion 19, and a portion in which the base portion 15A of the rod pressing member 15 corresponds to the spherical body portion 19 in an opposing manner. The spherical body portion 19 is swingably attached to the pair of engagement recess portions 21, 21.

Accordingly, in a state in which the spherical body portion 19 of the shank portion 3 is lightly clamped by the pair of engagement recess portions 21, 21 of the connector main body 11, it is possible to swing the connector main body 11 in a desired direction with respect to the shank portion 3. On the other hand, when the pair of engagement recess portions 21, 21 firmly clamp and fix the spherical portion 19, the connector main body 11 is fixed to the shank portion 3.

In order to clamp and fix the rod 7 by the rod supporting portion 9 and the rod pressing portion 13, and clamp and fix the spherical body portion 19 by the pair of engagement recess portions 21, 21, a protruding portion 11B is provided with a pressure fixing device 23 for pressing and fixing the rod pressing member 15 in a direction of the rod supporting portion 9. As one embodiment of the pressure fixing device 23, in the present embodiment, a fixing screw freely pressing the rod pressing member 15 by a distal end thereof is screwed into the connector main body 11.

Accordingly, the rod 7 can be fixed and supported by the rod supporting portion 9 and the rod pressing portion 13, by fastening the fixing device (the pressure fixing screw) 23, and the connector main body 11 can be fixed to the shank portion 3.

Figure 5A:
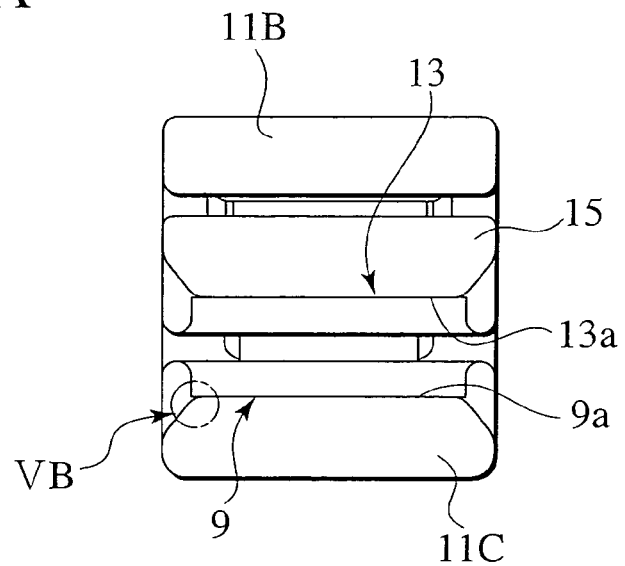
FIG. 5A is a right side view of the rod connector according to the embodiment of the present invention.
Figure 5B:
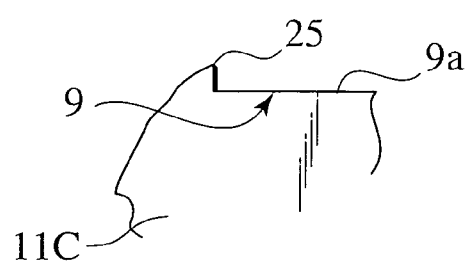
FIG. 5B is a partly enlarged view of FIG. 5A.
Figure 6:
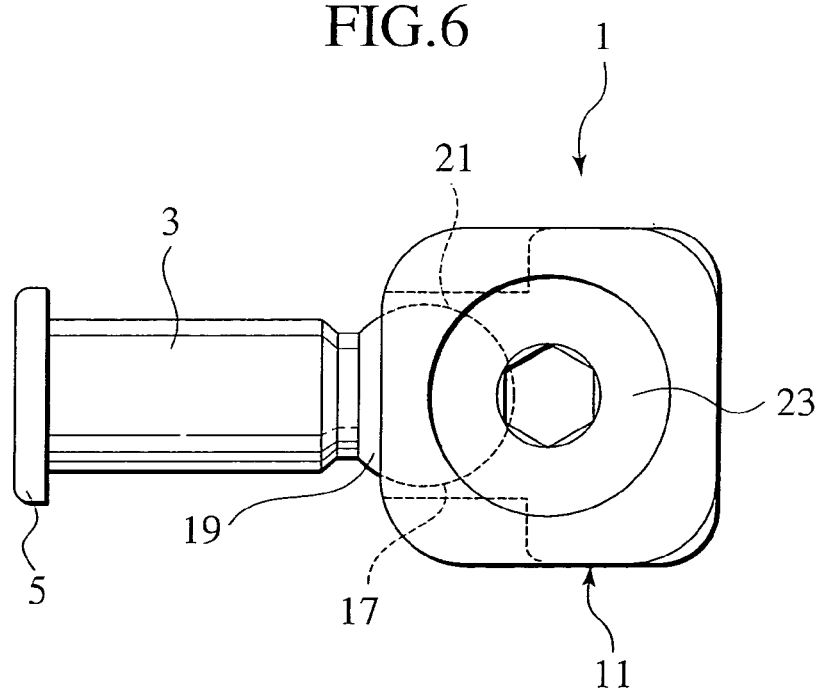
FIG. 6 is a plan view of the rod connector according to the embodiment of the present invention.

In order to fix and support the rod 7, small convex portions 25, 25 having a sharp distal end eating into the rod 7 are provided in a protruding manner in both end sides of the rod supporting portion 9 and the rod pressing portion 13 (both end sides of the rod 7 in a longitudinal direction), as shown in FIG. 5B. Further, a supporting surface 9a is provided between the convex portions 25, 25 of the rod supporting portion 9 (FIG. 5B shows only the small convex portion 25 of the rod supporting portion 9). In the same manner as the supporting surface 9a, a supporting surface 13a is provided between the convex portions (not shown) These supporting surfaces 9a, 13a are formed as a rough surface, for example, by a sand blast or the like.

Accordingly, when the rod 7 is firmly clamped and gripped by the rod supporting portion 9 and the rod pressing portion 13, and a stress is concentrated near a distal end by the sharp distal end of the small convex portions 25, so that the distal end of the convex portions 25 eats into the surface of the rod 7 so as to generate a scratch, and the supporting surface 9a (13a) of the rough surface is brought into contact with the rod 7. Therefore, it is possible to prevent the rod 7 from moving in the axial direction and it is possible to prevent the rod 7 from rotating around an axis thereof.

In this case, in some difference in diameter of the rod 7, there is a case that the engagement state between the engagement recess portions 21, 21 in the connector main body 11 and the rod pressing member 15, and the spherical body portion 19 of the shank portion 3 is slack, at a time of firmly gripping and fixing the rod 7 by the rod supporting portion 9 and the rod pressing portion 13. Further, on the contrary, there is a case that the clamping and fixing state of the rod 7 by the rod supporting portion 9 and the rod pressing portion 13 becomes slack, in a state in which the engagement state between both the engagement recess portions 21 and the spherical body portion 19 is a firm fixing state.

In the case mentioned above, the rod supporting portion 9 is replaced by the connector main body 11 formed in the circular arc curved surface corresponding to the diameter of the rod 7, and the rod pressing portion 13 is replaced by the rod pressing member 15 formed in the circular arc curved surface corresponding to the diameter of the rod 7, whereby it is possible to simultaneously achieve a clamping and fixing of the rod 7 and a fixing and integrally forming of the connector main body 11 with respect to the spherical body portion 19 of the shank portion 3. In other words, it is possible to correspond to various rods 7 having various diameters by replacing both of the connector main body 11 and the rod pressing member 15 with respect to the shank portion 3.

According to the rod connector of the present embodiment, it is possible to adjust a position of the shank portion 3 in an axial direction with respect to the screw screwed into the vertebra body so as to fix, and it is possible to adjust swing and rotation of the connector main body 11 in a desired direction with respect to the shank portion 3 so as to fix.

Accordingly, even in the case that an adjusting freedom of the rod connector is large with respect to the screw screwed and fixed to the vertebra and a slight displacement is generated in the screw fixing position, or even in the case that the rod 7 has a curve, an incline or the like, it is possible to easily correspond thereto, and it is possible to always property support and fix the rod 7, so that the conventional problems mentioned above can be solved.

In this case, the present invention is not limited to the embodiment mentioned above, and can be applied to the other aspects. In other words, the same effects can be achieved in a structure in which the connector main body 11 and the spherical body portion 19 can be fixed by a locking screw, the rod pressing member 15 is omitted, and the rod 7 is directly pressed to the rod supporting portion 9 by the pressure fixing device 23.

What is claimed is:

1. A rod connector, comprising:
    a connector main body swingably attached to a shank, said connector main body comprising a recess configured to engage part of a spherical end portion of the shank, part of said spherical end portion extending outside of said recess in a direction towards the shank;
    a rod supporting portion provided in the connector main body and configured for supporting a rod; and
    a pressure fixing device for pressure fixing the rod to the rod supporting portion of the connector main body, wherein the rod supporting portion comprises convex portions at both ends of the rod supporting portion, said convex portions including a first convex portion comprising a sharp distal end provided at a first end only of the rod supporting portion and configured to be embedded into the rod, and a second convex portion comprising a sharp distal end provided at a second end only of the rod supporting portion and configured to be embedded into the rod.

2. The rod connector according to claim 1, said rod supporting portion between said convex portions further comprising a rough surface.

3. The rod connector according to claim 1, each convex portion further comprising a convex surface, and
    each sharp distal end including a surface substantially normal to said rod supporting surface.

4. The rod connector according to claim 1, said rod supporting portion having a longitudinal direction for supporting the rod along the longitudinal direction of the rod, and each convex portion further comprising a convex surface projecting in the longitudinal direction of said rod supporting portion, said convex portions projecting away from each other.

5. A rod connector, comprising:
a connector main body swingably attached to a shank, said connector main body comprising a recess configured to engage part of a spherical end portion of the shank, part of said spherical end portion extending outside of said recess in a direction towards the shank;
a rod supporting portion provided in the connector main body and configured for supporting a rod; and
a pressure fixing device for pressure fixing the rod to the rod supporting portion of the connector main body, wherein the rod supporting portion comprises convex portions at both ends of the rod supporting portion, each convex portion comprising a sharp distal end extending in a smooth, continuous, sharp ridge along a circumferential direction of the rod supporting portion and configured to be embedded into the rod.

* * * * *